United States Patent [19]

Yankeelov, Jr. et al.

[11] Patent Number: 4,631,270
[45] Date of Patent: Dec. 23, 1986

[54] THERAPEUTICALLY USEFUL PSEUDOPEPTIDES, COMPOSITIONS CONTAINING THE SAME AND METHODS OF PREPARATION AND USE

[75] Inventors: John A. Yankeelov, Jr.; Kam-Fook Fok, both of Louisville, Ky.

[73] Assignee: Research Corporation, New York, N.Y.

[21] Appl. No.: 715,424

[22] Filed: Mar. 25, 1985

Related U.S. Application Data

[63] Continuation of Ser. No. 962,100, Nov. 20, 1978, abandoned, which is a continuation-in-part of Ser. No. 868,626, Jan. 11, 1978, abandoned.

[51] Int. Cl.$^4$ .................. A61K 37/43; C07K 7/12; C07K 7/20; C07K 7/06
[52] U.S. Cl. .................. 514/15; 514/17; 514/19; 514/800; 514/809; 530/328; 530/313; 530/302
[58] Field of Search .................. 260/112.5 R; 514/15, 514/17, 19, 800, 809; 530/302, 313, 328

[56] References Cited

U.S. PATENT DOCUMENTS 3,973,006  8/1976  Ondetti .................. 260/112.5 R

OTHER PUBLICATIONS

J. Med. Chem., vol. 6 (1962) 136–141, Karlan, et al.

*Primary Examiner*—Delbert R. Phillips
*Attorney, Agent, or Firm*—Scully, Scott Murphy and Presser

[57] ABSTRACT

Therapeutically useful pseudopeptides characterized by the replacement of at least one peptide group, both in a naturally occurring peptide or protein by a thiomethylene group are useful in the treatment of various metabolic malfunctions.

13 Claims, 12 Drawing Figures

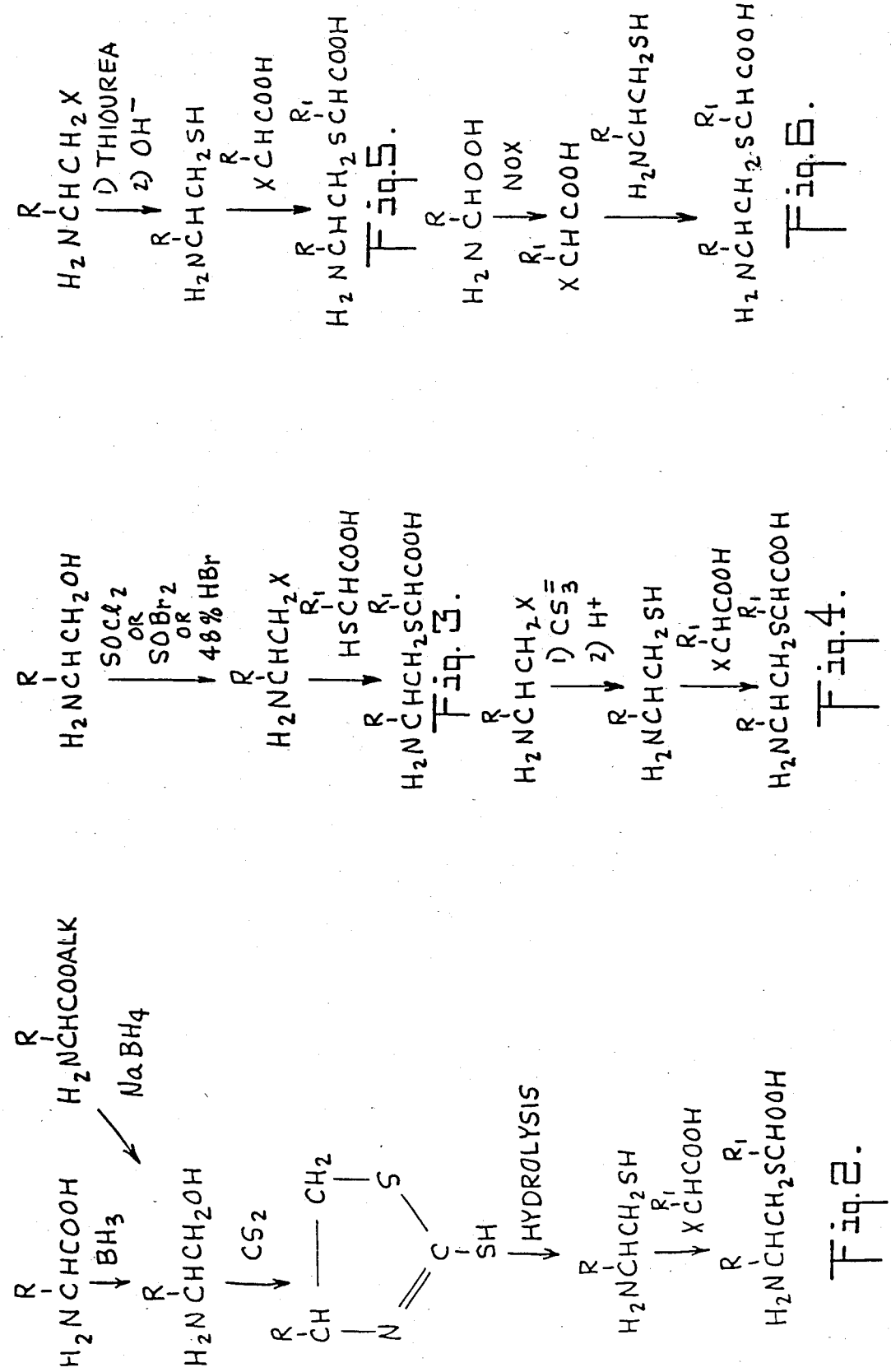

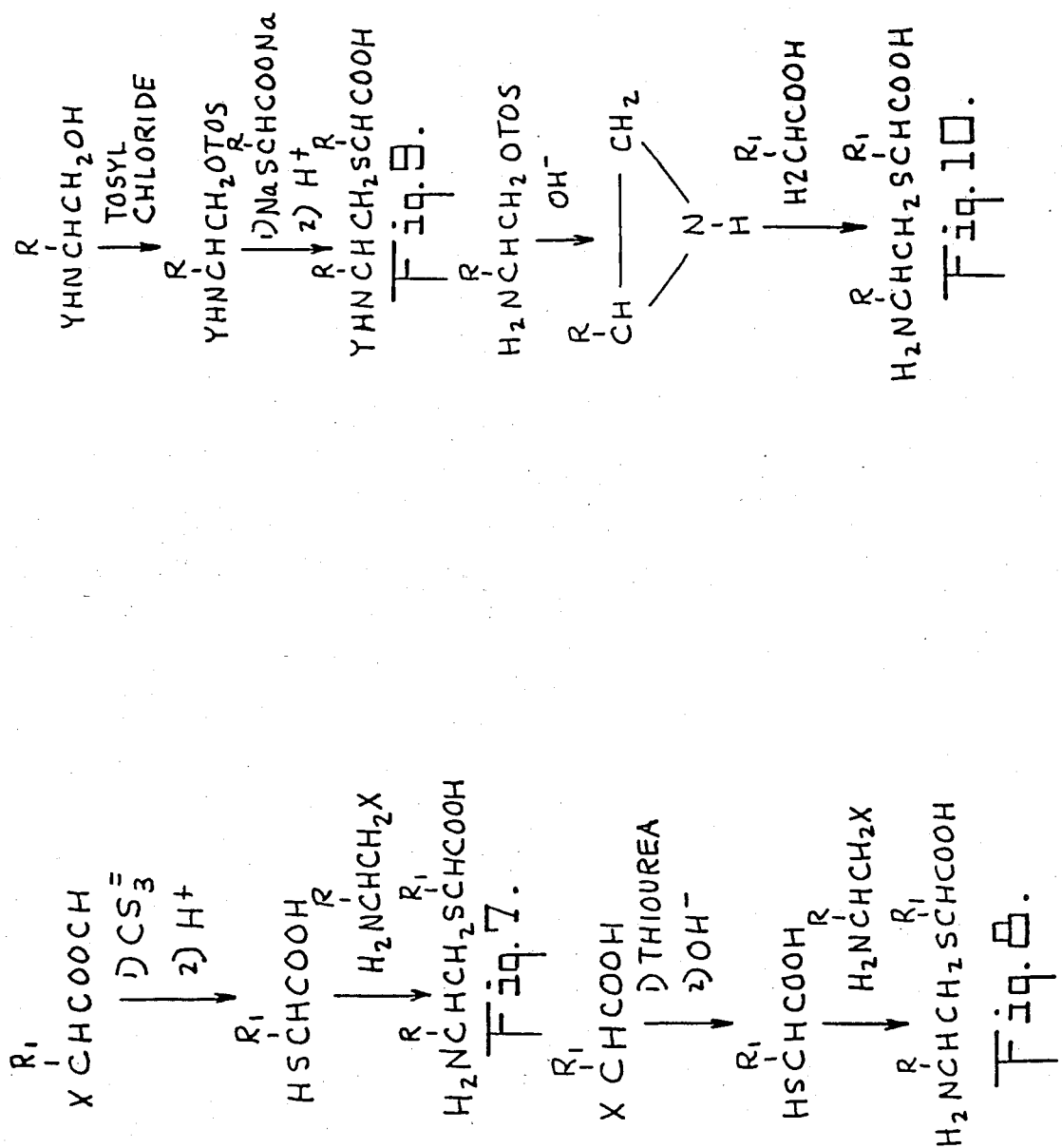

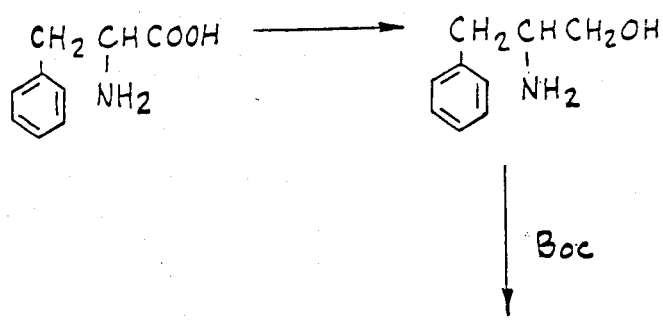
Fig.11.
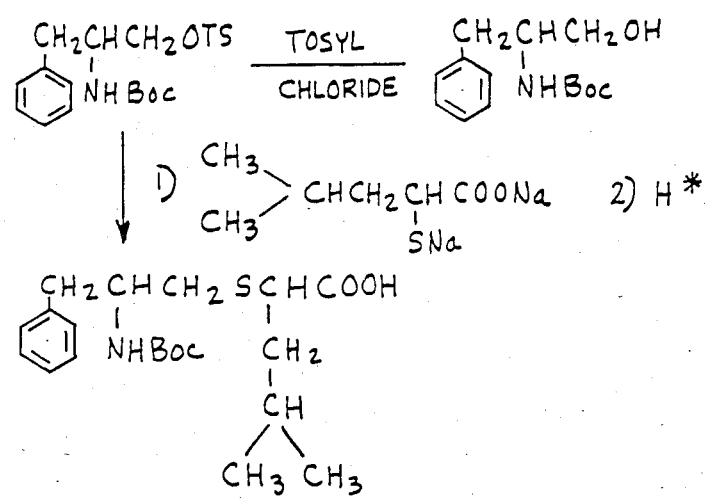
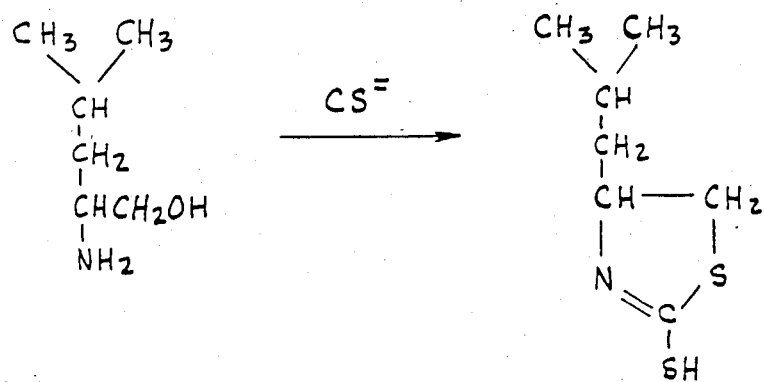
Fig.12.
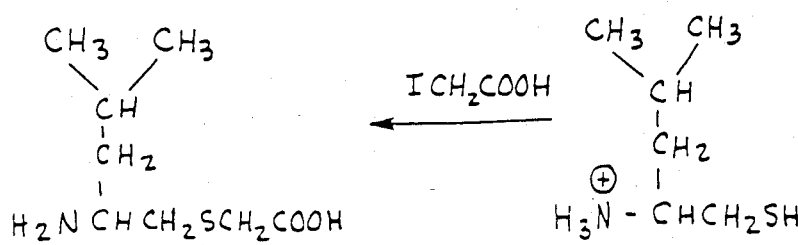

THERAPEUTICALLY USEFUL PSEUDOPEPTIDES, COMPOSITIONS CONTAINING THE SAME AND METHODS OF PREPARATION AND USE

RELATED APPLICATION

This application is a continuation of Ser. No. 962,100, filed Nov. 20, 1978, which was a continuation-in-part of Ser. No. 868,626, filed Jan. 11, 1978, both now abandoned.

BACKGROUND OF THE INVENTION

Most physiological functions of the mammalian body are controlled by enzymes or hormones which may be generically described as physiological catalysts. Many of these involve metabolic reaction sequences, one or more steps of which involve hydrolytic cleavage of a protein. For example, in the sequence of reactions which results in the coagulation of blood, a critical step is the conversion of prothrombin to thrombin. This conversion is catalyzed by the enzyme Factor $X_a$, which stimulates the hydrolysis of arginylthreonine and arginylleucine depeptide units in the prothrombin molecule.

If these proteolytic control cleavage steps go awry, there may be unfortunate pathological results. For example, the body protects itself from the danger of circulating blood clots by dissolving them. A part of the reaction sequence which ultimately effects such dissolution is the conversion of plasminogen to plasmin which is triggered by the enzyme urokinase. Excess urokinase activity can result in the formation of too much plasmin, and this, in turn, can lead to inability to form clots. Consequently, the body is unable to protect itself from hemorrhage. There are many other examples of such metabolic malfunctions.

THE INVENTION

This invention provides a procedure for alleviating the harmful effects of such imperfections by providing therapeutic agents which masquerade as one of the participants in metabolic reactions involving proteolysis. These disguised molecules function as unnatural substrates which bind the natural catalysts or catalysts which bind the natural substrates and mitigate the results of high concentration or hyperactivity of the natural substance.

More specifically, the therapeutic agents of this invention masquerade as one partner in a proteolytic pair. A specific agent may masquerade as a catalyst, e.g., an enzyme or a hormone, or it may masquerade as a substrate for an enzyme. In any event the pseudopeptide, or unnatural partner, binds the natural partner and minimizes its participation in the natural metabolic pathway. If, for example, the pseudopeptide is a segment of a natural substrate for a specific enzyme; that enzyme, while bound to the unnatural substrate, is not available to perform its usual function. For instance, the production of dangerous amounts of plasmin can be inhibited by providing a plasminogen surrogate which binds urokinase.

The invention will be better understood by reference to the figures in which FIG. 1 is a drawing illustrating the spatial similarity of glycylglycine and its counterpart in which the peptide bond is replaced with a thiomethylene group. FIGS. 2 through 10 illustrate various procedures for preparing products of the invention. FIGS. 11 and 12 illustrate the preparation of pseudo phenylalanylglycine and pseudo leucylglycine utilizing combinations of the processes shown in certain of the previous figures.

The compounds of this invention are pseudopeptides containing up to ten or more bonds joining amino acid segments, and at least one linkage between amino acid segments is replaced with a thiomethylene group so as to provide a pseudopeptide at least one portion of which may be represented by the following partial structure:

wherein R and $R_1$, which may be the same or different, are side chains of amino acid residues. The balance of the bonds between amino acid segments are peptide bonds. In the structure, the open valences on the nitrogen atom will normally be completed by a hydrogen atom or the carbon atom of a peptide bond through which another amino acid is joined to the structure. Similarly, the open bond on the carbon atom could be completed by an hydroxyl group or by connection to the nitrogen atom of a peptide bond.

Thus, for example, the above structure might be completed by union of its amino terminus with the carboxyl group of glycine and its carboxyl terminus with the group of alanine. The resulting pseudopeptide would have the structure:

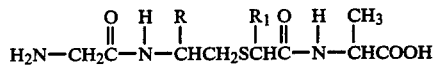

The union might also involve omega amino, carboxyl or guanadino groups as in lysine, glumatic acid or arginine. It might also involve an imino group of proline or hydroxyproline. The important point is that the resulting structure is one in which one chemically replicates one member of a proteolytic pair in substantially all respects except the presence of at least one thiomethylene linkage.

In addition, to bein closely related chemically to the naturally occurring materials, the products of this invention are also substantially isosteric with their natural counterparts as well as being substantially equivalent in basicity configuration.

The principal reason for the close duplication of these important physical and chemical parameters of the natural product is the close relationship of the thiomethylene and the peptide groups. This relationship is clearly illustrated in FIG. 1 of this application. From a study of the figure it will be seen that the carbon, hydrogen, nitrogen and oxygen bonds on both sides of the peptide and thiomethylene groups have substantially the same spatial relationship, and that the thiomethylene group is approximately the same size as the peptide group. The infrastructure of the peptide group and the thiomethylene group are also very similar so that the substitution of a thiomethylene group for a peptide group of a natural product does not materially affect such factors as charge distribution, dielectric constants, and ability to become hydrated. Accordingly a pseudopeptide of this invention is capable of masquerading for its natural counterpart and affecting in a controlable fashion those reactions in which the natural product is normally involved.

Two of the most important results which arise from the close similarity of the products of this invention and their natural products are (1) they can be used as therapeutic agents to control the rate of naturally occurring metabolic reactions involving proteolysis by their ability to substitute for their natural counterpart and (2) they are non-toxic and non-mutagenic.

The pseudopeptide illustrated above is pseudotetrapeptide containing only one thiomethylene linkage. For some purposes, smaller pseudopeptides may be advantageous, and for others, it may be preferred to utilize pseudopeptides containing as many as eight or more amino acid segments. The reasons for these variations will be apparent from a consideration of the simple lock and key analogy often used in describing protein-protien interactions such as the action of a protein enzyme on a protein or peptide substrate. If the protein or peptide substrate is considered the key and the enzyme the lock, the geometrical configuration of the two structures must complement each other or the key will not fit the lock, and no reaction will take place.

If the pseudopeptide now is to take the place of the lock, it must have sufficient geometric structure so that the key fits. This requirement may be satisfied by a pseudodipeptide, but often a higher molecular weight pseudopeptide may be more sastisfactory.

The compounds of this invention, as will be recognized by those skilled in the art, are amphoteric in nature, and may be formed into pharmaceutically acceptable acid addition and metallic salts. Such salts are within the scope of the invention. As the description proceeds, it will be apparent to those skilled in the art that a number of derivatives of the therapeutically active substances can be prepared. Simple derivatives include esters and amides. More complex derivatives include products formed by reactions with free functional groups on the amino acid residues, for example, the hydroxyl group of tyrosine. These, too, are within the ambit of the invention.

Normally, the compounds of this invention will be based upon L-amino acides. However, in certain instances, it may be advantageous to utilized the D-form of the acid. Accordingly, both forms are within the scope of the invention.

The following definitions of some of the words and terms used in the description of this invention may assist in understanding.

Pseudopeptide—a peptide containing amino acid residues in which at least one of the normal peptide bonds has been replaced by a thiomethylene group.

Amino acid residue—that portion of an α-amino acid molecule which remains after removal of the hydroxyl portion of the carboxyl group and a hydrogen atom of the amino group in the formation of a peptide bond. It will be readily understood from the description of the reaction sequences used to form the compounds of this invention that it is not necessary to employ an α-amino acid as a starting material. This will present no difficulty in visualizing the meaning of the term "amino acid residue" to those skilled in the art.

Amino acid side chain—that portion of an α-amino acid which is joined to the α-carbon atom in addition to the amino group, or in the case of proline or hydroxproline, the imino group. The term includes, for example, the hydrogen of glycine, the benzyl group of phenylalanine, or the isobutyl group of leucine.

The pseudopeptides within the scope of this invention will, for convenience, be designated by the Greek letter Ψ (Psi) in place of a dash to indicate replacement of a peptide linkage by a thiomethylene linkage. Additionally, the standard abbreviations for the common amino acids will be employed. Thus, Gly - Leu, and Gly Ψ Leu are glycylleucine and pseudoglycylleucine, respectively. Their molecular formulas would be:

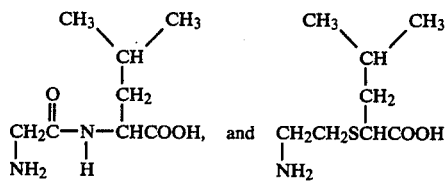

A typical pseudotetrapeptide within the scope of this invention containing only one thiomethylene linkage is:

Leu Ψ Leu - Val - Tyr

This compound, its pharmaceutically acceptable salts and derivatives are useful in the treatment of hypertension by inhibiting the conversion of angiotensin to angiotensin I and angiotensin II by the enzyme renin. Treatment of a patient with a pharmaceutical composition containing the pseudopeptide provides a masquerading substrate which competes with the natural substrate angiotensin for the available renin. To the extent that the renin becomes bound to the pseudopeptide, is it unavailable for the natural conversion. Therefore, the pseudopeptide serves as a useful therapeutic agent for the control of hypertension.

Other pathological conditions can also be treated with the pseudopeptides of this invention; the pseudopeptide employed and the metabolic pathway which is interrupted include:

Hypertension

Hypertension is a common medical problem. A key step in the regulation of blood pressure is the enzymatic cleavage of $\alpha_2$-globulin to yield angiotension I which in turn is cleaved to angiotension II. Angiotension II is a powerful pressor and blockages of its formation provides an effective therapeutic tool. The conversions involve cleaving Phe-His and Leu-Leu bonds. Introduction of Phe Ψ His and Leu Ψ Leu into selected pseudopeptides and administration of those pseudopeptides provides a block to the conversion of $\alpha_2$-globulin to angiotension II. The pseudopeptides and their derivatives which are useful for this type of block include: Ac-Phe Ψ His-Leu-Leu-Val-Tyr-Ser-OH; Ac-Phe-His-Leu Ψ Leu-Val-Tyr-Ser-OH and Ac-Phe Ψ His-Leu Ψ Leu-Val-Tyr-Ser-OH. Suitable methods of administration include parenteral, I.V., nasal aerosol and supository modes.

Corneal Ulceration

Corneal ulceration is a commonly encountered ophthalmological problem with a broad spectrum of etiologies including ocular burns, rheumatodial arthritis and infection. The ulceration results from the action of excessive production of collagenase during the healing process. The cornea is 70% collagen. Cleavage of collagen by collagenase is highly specific involving only Gly-Ile and a Gly-Leu linkages. The pseudopeptides required to control these destructive cleavages incorporate, therefore, Gly Ψ Ile and Gly Ψ Leu. Typical therapeutic agents of this invention incorporating the desired structures are:

Ac-Pro-Gln-Gly Ψ Ile-Ala-Gly-Gln-Arg-Gly-OEt

Ac-Pro-Cln-Gly Ψ Leu-Ala-Gly-Gln-Arg-Gly-OEt

Ac-Pro-Leu-Gly Ψ Ile-Ala-Gly-Leu-Arg-Gly-OEt

Ac-Pro-Leu-Gly Ψ Leu-Ala-Gly-Leu-Arg-Gly-OEt, the amide analogs thereof, or the parent compounds in which the carboxyl group of the glycine molecule is free. Treatment of the ulcerating cornea is done by topical application in isotonic acqueous. solution at approximately PH 7.4, several times daily.

Since it is known that the C-terminal Arg is removed when the peptide is in contact with plasma, it is useful to include Gln Ψ Arg or Leu Ψ Arg in the same peptide or a D Arg at the C terminal position. The resulting useful pseudopeptides are:

Ac-Pro-Gln-Gly Ψ Ile-Ala-Gly-Gln Ψ Arg

Ac-Pro-Gln-Gly Ψ Ile-Ala-Gly-Leu Ψ Arg, or the corresponding esters or amides. The Ile in the pseudo linkage may be replaced with Leu

Rheumatoid Arthritis

Rheumatoid arthritis is a syndrome afflicting millions of individuals. The destructive aspects of this disease includes the hydrolytic action of tissue collagenase on the collagen matrix of the afflicted joints. Since the generic enzyme of interest in this syndrome is the same as that for corneal ulceration, the therapeutic pseudopeptides are identical to those described for that affliction. A common clinical procedure with rheumatoid patients is the removal of excess synovial fluid from inflamed joints. Treatment of the patient involves injection of a sterile saline solution or suspension of the pseudopeptides in a volume of I ml or less replacing only a small fraction of the fluid withdrawn.

Anticoagulants

Large numbers of coronary patients receive anticoagulants as a precautionary measure to avoid the threat of thrombosis. Agents used are frequently vitamin K antagonists and, therefore, interefere with all known and unknown actions of vitamin K. A more specific interference with blood clotting is provided by blocking the conversion of prothrombin to thrombin by the action of proteolytic enzyme factor $\overline{X}_a$. This enzyme cleaves specifically at Arg-Thr (Residues 274–275) and Arg-Ile (Residues 323–324) of the prothrombin sequence. Interference with these cleavages by synthesis and administration of appropriate pseudopeptides provide highly specific blocking agents to the onset of clotting. These pseudopeptides contain Arg Ψ Thr and Arg Ψ Ile.

These pseudopeptides are:

Ac-Ile-Glu-Gly-Arg Ψ Thr-ser-Glu-OEt and

Ac-Ile-Glu-Gly-Arg Ψ Ile-Val-Glu-OEt.

Methods for administration include tablet, I.V., nasal aersol or swab and suppository modes.

Modulation Of Urokinase Action

The enzyme urokinase activates plasminogen to plasmin. This conversion is an important step in the control of thrombosis. Accordingly urokinase is widely used in therapy. An unfortunate side effect in urokinase therapy is bleeding. This invention provides for control of bleeding by attenuating the activity of urokinase through a specific inhibitor of the action of urokinase. Thus, when urokinase is unsuited to treatment as evidenced by bleeding the appropriate pseudodipeptides may be administered. The component pseudodipeptides are Arg Ψ Met and Lys Ψ Ser.

The completed pseudopeptides used in the block are:

Ac-Ser-Ile-Arg Ψ Met-Arg-Asp-Val-OEt and

Ac-Glu-Asn-Arg-Lys Ψ Ser-Ser-Ile-Ile-OEt.

Methods of administration include parenteral, I.V. nasal aerosol or swab and suppository modes. These preparations are also useful in treatment of hemophilia.

Control Of Destruction By Elastin In Emphysema

Individuals who are genetically deficient in $\alpha_2$-antitrypsin present a high risk for pulmonary emphysema. The $\alpha_2$-antitrypsin in the pulmonary circulation normally protects lung tissue against the action of elastase. Without this protection, the deficient individual suffers extensive pulmonary damage by the action of elastase. The most common peptide bond cleaved by the elastase in an Ala-Ala linkage. Accordingly, the pseudodipeptide incorporated in the inhibitor is Ala Ψ Ala. The resulting therapeutic peptides are Ac-Ala-Ala Ψ -Ala OEt and Ac-Ala-Ala-Ala Ψ Ala-OEt. The method of administration is by inhalation of an aqueous aerosol.

LHRH

Luteinizing hormone-releasing hormone (pGlu-His-Trp-Ser-Tyr-Gly-Leu-Arg-Pro-Gly-NH$_2$) is used for treatment of a variety of endocrine disorders which include loss or lack of fertility, proper function of the menstrual cycle and ovulation as well as male infertility. This hormone has a short biological half-life (2 min.) because of rapid destruction by proteolysis. A long-lived hormone, therefore, provides an important therapeutic instrument. The bonds subject to proteolysis are Gly-Leu, Tyr-Gly and Pro-Gly-NH$_2$. The required pseudodipeptide units required are Gly Ψ Leu, Tyr Ψ Gly and Pro Ψ Gly-NH$_2$. The long-lived hormones, therefore, are:

pGlu-His-Trp-Ser-Tyr Ψ
        Gly-Leu-Arg-Pro-Gly-NH$_2$ pGlu-His-Trp-Ser-Tyr-Gly-Leu-Arg-Pro Ψ
        Gly-NH$_2$ pGlu-His-Trp-Ser-Tyr Ψ Gly-Leu-Arg-Pro Ψ
        Gly-NH$_2$ pGlu-His-Trp-Ser-Tyr-Gly Ψ
Lev-Arg-Pro-Gly-NH₂

Modes of administration include nasal aerosol or swab, suppository, parenteral and I.V. methods in a vehicle of normal saline.

Anticoagulant-Block Of The Action Of Thrombin Or Fibrinogen

As described previously, anticoagulants are important therapeutic agents. Blood coagulation processes involve a complex cascade of activations by proteolytic enzymes which culminate in the cleavage of fibrinogen with thrombin to produce fibrin which spontaneously assembles to a soft clot. The point of thrombin cleavage in the A-α- chain is an Arg-Gly bond. Accordingly, the pseudodipeptide unit required for incorporation into the inhibitor is Arg Ψ Gly. The completed peptide inhibitor of thrombin action is:

Ac-Gly-Gly-Gly-Val-Arg Ψ Gly-Pro-Arg-Val-NH₂

Methods of administration include tablet, I.V., nasal aerosol or swab, and suppository modes.

Protection Against Peptic Ulcers

Pepsin is the dominant proteolytic enzyme found in gastric juice. Individuals who secrete excessive gastric fluid suffer ulceration due to proteolysis. Inhibition of proteolysis due to pepsin protects against enzymatic damage. The Phe-Phe linkage is especially prone to proteolysis by pepsin. Accordingly, the pseudodipeptide required for synthesis is Phe Ψ Phe.

The therapeutic inhibitor is:

Ac-Ala-Ala-Phe Ψ Phe-NH₂

Administration of this substance is accomplished orally in tablet or liquid form in combination with antiacids.

Pseudopeptides Of Tuftsin

Medical syndromes exist in which cells of the patient are essentially incapable of phagocytosis or pinocytosis. A class of phagocytosis-stimulating peptides which are therapeutically useful contain basic and hydroxy amino acids in specific patterns. These agents fall into structural patterns of the type H-B-Pro-B', where H indicates a position occupied by a hydroxy amino acid (Thr or Ser) and B and B' represent basic amino acids such as Arg, Orn or Lys. Plasma is known to have carboxypeptidase B activity and kidney is known to contain aminopeptidase activity. Pseudotuftsins, therefore, containing Pro Ψ Lys, Pro Ψ Arg, Ser Ψ Lys and Ser Ψ Arg (for example) have a longer biological half life than the normal peptide. Exemplary pseudotuftsins, therefore, include Thr-Lys-Pro Ψ Arg, Thr Ψ Lys-Pro-Arg and Thr Ψ Lys-Pro Ψ Arg. The Arg may be replaced with Orn. These pseudotuftsins have varying degrees of resistance to proteolysis.

Methods of administration include tablet, injection and aqueous oral procedures.

Insulin Of Extended Biological Half Life

Insulin is widely used in the treatment of diabetics. Insulin is inactivated by removal of the C-terminal octapeptide by trypsin-like activity. Accordingly, pseudoinsulins may be prepared which are resistant to proteolysis by incorporating Cys Ψ Asp at positions 20–21 in the A chain of human insulin and/or by replacing residues 22 and 23 in the B chain of insulin by Arg Ψ Gly. Coupling (oxidation) of the chains prepared by solid phase synthesis provides an insulin resistant to proteolysis. The resulting pseudoinsulins may be administered in precisely the same manner as natural or synthetic human insulin.

Enkephalins, Endorphins

Recently the structures of endogenous opiate peptides have been discovered and explored. These substances (enkephalins and β-endorphins) have pain relieving qualities similar to opium. Loss of biological activity of Leu₅-enkephalin, which has the structure Tyr-Gly-Gly-Phe-Leu, is due to cleavage of the Tyr-Gly bond. Replacement of the Tyr Ψ Gly produces and analog of longer biological half-life and, therefore. of enhanced therapeutic value, The final pseudo enkephalin would be Tyr Ψ Gly-Gly-Phe-Leu. The Leu may be replaced with Met.

A similar approach can be applied to the stabilization of β-endorphins by substituting a Met Ψ Thr linkage in the β-endorphin. Leu Ψ Thr may be equally effective.

Modes of administration would be primarily, I.V. but intranasal and intrarecta 1 administration are also possible.

Inhibition of Acrosin

Acrosin is the key enzyme found in spermatozoa. The function of this trypsin-like enzyme is to facilitate penetration of the ovum during fertilization. Interruption of the action of acrosin prevents fertilization. The inhibitory substance here is Benzoyl-Arg Ψ Gly OEt. The pseudodipeptide would be Arg Ψ Gly.

This inhibitor of fertilization is used in an intravaginal foam similar to Delfin.

Long-Lived Oxytocin

Oxytocin causes uterine contraction and is used in obstetrics when induction of uterine contraction is desired. The structure of oxytocin is:

```
 NH₂
  |
 Cys—Tyr—Ile
  |         |
  S         |
  |         |
  S         |
  |         |
 Cys—Asn—Gln
  |
 Pro—Leu—Gly—NH₂
```

The pseuduo-oxytocin of this invention having a longer biological half life is:

```
 NH₂
  |
 Cys—Tyr ΨIle
  |         |
  S         |
  |         |
  S         |
  |         |
 Cys—Asn—Gln
  |
 Pro—Leu Ψ Gly—NH₂
```

The pseudodipeptides which would be employed are:

Tyr Ψ Ile and

Leu Ψ Gly-NH₂

Long-Lived Vasopressin

Vasopressin is used in surgical shock as an adjuvant in elevating blood pressure. It is also used in the management of delayed postpartum hemorrhage and at delivery to overcome uterine inertia.

The structure of vasopressin is:

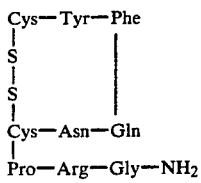

The pseudodipeptides which are useful in accordance with this invention are:

Arg Ψ Gly-NH₂

Tyr Ψ Phe

Pro Ψ Arg

A pseudovaspressin incorporating these products is:

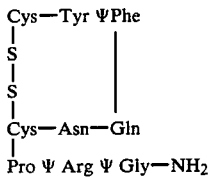

The product can be administered intravenously or intranasally.

All of the above physiological conditions are grouped, for purposes of this description, as metabolic malfunctions—simply as a matter of convenience. Some of them, however, are not, in fact, metabolic aberrations, although they do involve metabolic reactions. For example, the relief of pain is not a question of a metabolic pathway gone astray.

One common feature of all of the conditions described above is that at some point in the succession of reactions which results in the condition, a substrate containing a natural peptide bond is cleaved. The feature of this invention is that the total production of the products of that cleavage is reduced by bringing to the reaction site a pseudopeptide which competes for either the substrate or the catalyst involved in the reaction by masquerading for one of the participants.

Since the development of the genetic code, it has become clear that polymers such as DNA, RNA and proteins, as well as peptides are information containing products. In the case of nucleic acids, the information resides in the sequential appearance of purine and pyrmidine bases. Similarly, when this information is "translated" to the level of protein or peptide structures, it is the amino acid side chains which impart the distinctive characteristics of the protein or peptide. The function of the peptide backbone is largely relegated to that of a connecting structure. For example, polyglycine is essentiall devoid of information. It is the appearance of the unique side chains brought into play by the genetic code that dictate the manner in which a peptide or protein folds, and therefore the spatial relationship between the various atoms and molecular segments, particularly the side chains on the basic structure. The three dimensional structure which results permit cooperative interaction between various proteins, for example enzymes and substrates and thus determinestheir biological activities.

The problem solved by this invention is the construction of a protein or peptide like structure with substantially the same mclecular geometry as its natural counterpart. The problem has been solved by replacing a peptide bond with a thiomethylene bond. Products built around such thiomethylene bonds have essentially the same molecular geometry as natural products. They are capable of participating in the same type of reaction. However, since the thiomethylene bond is resistant to hydrolysis, the effect of increasing the concentration of the pseudopeptide in the presence of the natural product and it natural coreactant is to decrease the concentration of the product of the normal reaction because of the fact that the pseudopeptide has the right geometrical configuration to bind the natural coreactant. The bound materials are not readily cleaved because of the hydrolytic resistance of the pseudopeptide.

The unusual advantage of this invention is the substantially complete predictability of the results. Once the essential feature of the natural reaction is known, a pseudopeptide can be constructed with confidence that it will be effective. It is known, for example that an enzyme and a substrate react by a process which includes binding at specific peptide bonds on each reactant, the reaction can be controlled by treatment with a pseudopeptide which replicates the particular section of the enzyme or the substrate containing the peptide bond except that the peptide bond is replaced with a thiomethylene group. It may be necessary to conduct some conventional studies to determine the best method of administration or other parameter using ordinary techniques known to those skilled in the art. The basic reaction however, is predictable with assurance.

The products of this invention are useful mammalian therapeutic agents and may be effective to inhibit hydrolytic cleavage of protein or peptide substrates at extremely low levels. The physician or veterinarian will determine the dosage which will be most suitable for a particular application. It may vary from patient to patient depending on the size of the patient, the condition under treatment and other factors which are readily evaluated by those skilled in the art. For continuous administration over extended periods to individuals with more or less permanent metabolic abnormalities, the products will normally be provided in various dosage forms varying from relatively large, to build up a prompt blood level, to relatively small to maintain an effective level. For intermittent treatments to combat acute or chronic problems, various dosage forms may be provided. The products may be administered at very high levels, even up to two or more grams per day. Normally, they will be provided in dosage units containing about 250 mg of the active ingredient and the number of units appropriate to the condition under treatment can be prescribed per day.

The products of this invention may be administered alone but will generally be administered with pharmaceutically acceptable, non-toxic carriers, the proportions of which are determined by the suitability and chemical nature of the particular carrier, the chosen route of administration, and standard pharmaceutical practice. For example, in dealing with certain abnormalities or in maintaining therapeutically effective levels in the blood or tissues, they may be administered orally in the form of tablets or capsules containing such excipients as starch, milk sugar, certain types of clay, etc. They may be enteric coated so as to be more resistant to the acid and digestive enzymes of the stomach. For intravenous and intramuscular administration, they may be used in the form of a sterile solution containing other solutes, for example, enough saline or glucose to make the solution isotonic.

It is a particular advantage of the products of this invention that unlike many peptide bond-containing therapeutic products, they can be administered orally because they have increased resistance to enzymatic hydrolysis by the enzymes of the lower digestive tract. Because of their amphoteric nature, they may be adsorbed for oral administration on non-toxic ion exchange resins which may be either anionic or cationic to achieve slow release either in the stomach or the intestines or both. Furthermore, adsorption on these resins makes them all the more resistant to enzyme destruction.

Another advantage arising from the amphoteric nature of the products of this invention is that, as discussed above, they can be utilized in the form of pharmacologically acceptable salts which may be either metallic salts or acid addition salts. These salts have the addvantage of water solubility and are particularly useful for parenteral administration. The metallic salts, especially the alkali metal salts, are relatively stable and for that reason are preferred over acid addition salts. The sodium salts are especially preferred because of their ease of preparation.

The acids which may be used to prepare the pharmacologically acceptable acid addition salts of this invention are those containing non-toxic anions and include, for example, hydrochloric, sulfuric, phosphoric, acetic, lactic, citric, tartaric, oxalic, succinic, maleic, gluconic, saccharic, and similar acids.

Any of a wide variety of non-toxic derivatives of the pseudopeptides of this invention can be usefully employed. The pharmacologically acceptable salts have been mentioned above. Amides, esters, acylated derivatives and others can also be utilized.

Other useful derivatives may be obtained by modifying the free functional groups on the pseudopeptide backbone, for example, free hydroxyl groups or free amino groups. One very convenient class of derivatives is the class in which a free hydroxyl group, for example, the free hydroxyl group of threonine or tyrosine is esterified with an alkanoyl or alkenoyl group containing up to eighteen or more carbon atoms. Alternatively, an amino group, for example, the amino group of threonine or lysine, can be acylated with an alkanoyl or alkenoyl group containing up to about eighteen carbon atoms. In both instances, the preferred derivatives are those in which the derivatizing groups contain from eleven to eighteen carbon atoms because the longer hydrocarbon chains impart increased lipid solubility to the molecules and enhance their transport across cell barriers.

Both types of derivatives may be prepared directly from the pseudopeptide, but are preferably prepared by incorporation during synthesis by reaction of an amino acid with the selected group, for example, the alkanoyl group already in place.

The compounds of this invention have a number of special features. One of the most important from the point of view of their therapeutic utility is the close configurational and chemical analogy between them and the natural compounds they are designed to replace. For this reason they may be utilized with minimum danger of antigenic reaxtions. Additionally, they appear to have little or no toxicity. Further, they can be metabolized and excreted without danger.

The natural substrates which the pseudopeptides of this invention are designed to replace, in the course of performing their usual physiological functions are hydrolyzed at a specific natural peptide bond site. The amino acid segments on either side of this site will be known. The pseudopeptide will normally be designed to include a partial structure in which the natural site is replaced with a thiomethylene group, and this partial structure will have on at least one side still further partial structure which is similar to the corresponding structure of the natural substrate.

One example of the low toxicity of the compounds of this invention is the results achieved with mice on treatment with Gly Ψ Leu. In the test Swiss Wistar mice were injected I.P. with Gly Ψ Leu at the dose levels indicated below. Five mice were tested at each dose level. In no case did any of the mice show any signs of acute toxicity. The behavior of the animals was observed closely for 7 days after injection. In no case were any adverse effects noted.

TABLE 1

| Weight Gains of Swiss Wistar Mice (N = 5) Injected with Gly Ψ Leu | |
|---|---|
| Dose Level | % Wt. Gain after 3 Days |
| 44 mg/Kg | 17 |
| 94 mg/Kg | 19 |
| 208 mg/Kg | 20 |
| 432 mg/Kg | 23 |
| Saline Control | 18 |

Possible mutagenic effects of pseudodipeptides were examined two ways. One possible route for a metabolic complication is via the action of methionine adenosyl transferase (MAT). Ethionine (which contains a thiomethylene linkage) is known to be both a carcinogen and a substrate for MAT. While the specificity requirements for MAT are stringent, the possibility existed that Gly Ψ Leu might be either a substrate or acompetitive inhibitor. As ividenced below, data obtained using the assay of Hoffman, Arch. Biochem and Biophys 179,136 (1977), reveals that neither Gly Ψ Leu nor Gly Ψ D-Leu has a measurable effect on MAT activity.

TABLE 2

| Effect of Gly Ψ Leu and Gly Ψ D-Leu on MAT | | | |
|---|---|---|---|
| | Substance | Concentration | Counts/Min transferred |
| Expt I | None | — | 15,760 |
| | Gly Ψ Leu | 12 mM | 16,620 |
| | Gly Ψ D-Leu | 12 mM | 16,760 |
| Expt II | None | — | 7,380 |
| | Gly Ψ Leu | 80 mM | 7,990 |
| | Gly Ψ D-Leu | 80 mM | 7,710 |

The mutagenicity of Gly Ψ Leu and Gly Ψ Ile was examined by a variation of the Ames test using repair-deficient strains of *Bacillus subtilis.*

The results shown in Table 2b indicate that neither Gly Ψ Leu nor Gly Ψ Ile behaves as a mutagen.

TABLE 2b

Mutagenicity Test Results

| Compound | Concentration | Growth Inhibition of Bacterial Strains in mm | | | | |
|---|---|---|---|---|---|---|
| | | Wild type | MC-1 | Hcr-9 | FB-13 | Pol A |
| Gly Ψ Leu | 0.1 M | 0 | 0 | 0 | 0 | 0 |
| Gly Ψ D-Ile | 0.1 M | 0 | 0 | 0 | 0 | 0 |
| Gly Ψ Ile | 0.1 M | 0 | 0 | 0 | 0 | 0 |
| Gly Ψ D-Ile | 0.1 M | 0 | 0 | 0 | 0 | 0 |
| Chloracetaldehyde | 0.6 M | 8 | 16 | 4 | 1 | 5 |

The specific procedures by which these tests were conducted are described in the following references:

1. Laumbach, A. D., Lee, S., Wong, J., and Streips, U. N., Studies on the Mutagenicity of Vinyl Chloride Metabolites and Related Chemicals. In: The Prevention and Detection of Cancer, Part 1, Prevention, Vol 1, Etiology, Edited by H. E. Nieburgs, Marcel-Dekker, Inc., New York (1977).

2. Kada, T., Tutikawa, K. and Sadaie, Y., Mutation Research 16 (1972), 165.

A number of procedures are available for the synthesis of the pseudopeptides of this invention. These are illustrated in FIGS. 1 through 12. In the figures R and $R_1$ are amino acid side chains as described above, ALK is an alkyl group containing up to five carbon atoms, X is halogen, Y is an amino blocking group and TOS is the tosyl group.

Those skilled in the art will recognize that several of the reaction sequences illustrated in the figures are based on the formation of a thiomethylene joining group by reaction of a primary halide with a secondary thiol or a secondary halide with a primary thiol. The various synthesis differ one from the other in the methods by which the critical reactants are prepared.

FIG. 2 illustrates a synthesis in which a primary thiol prepared through an intermediate mercapto thiazoline is reacted with an alpha-halocarboxylic acid which is a secondary halide.

For this synthesis the starting materials are amino acids which are reduced to form amino alcohols. A number of amino alcohols are known, and are available commercially. Others can be produced by reduction with borane in accordance with the procedure described by Yoon et al. in the Journal of Organic Chemistry, Vol. 38, No. 16, page 2786 (1973).

Generally, the procedure is one in which the amino acid to be reduced is contacted with borane, usually a molar excess of borane in an ether type solvent. The preferred solvent is tetrahydrofuran. The reaction temperature may be from about 15° C. to 40° C. over a reaction period which may vary from one-half hour to as long as twenty-four hours.

Any of a variety of isolation procedures can be utilized to obtain the reaction product. A suitable procedure is to decompose the excess reducing agent by the addition of cold water which may be diluted with a small amount of solvent.

Conversion of the amino alcohol to the desired mercaptothiazoline is effected in a reaction inert organic solvent in the presence of a strong alkaline reagent utilizing carbon disulfide as the cyclizing reagent. Typically, a molar excess, e.g. up to about a 30% molar excess of carbon disulfide, will be employed to ensure as complete a reaction as possible. The most convenient alkaline reagents are alkali metal hydroxides, such as sodium or potassium hydroxides. Any of a variety of reaction inert polar organic solvents may be employed. The presently preferred are lower aliphatic alcohols, particularly methyl and ethyl alcohols.

The reaction temperature may vary from approximately 30° C. to 45° C. under standard atmospheric conditions. Reaction is normally completed at the end of from about six to twelve hours.

The desired product is readily recovered by simple evaporation of the carbon disulfide and of the solvent. The residue is washed with cold dilute acid, e.g., 2% aqueous hydrochloric acid. It may be recrystallized for purification if desired, utilizing, in most instances, a 1:1 mixture of water and alcohol.

While borane is the presently preferred reducing agent, other reducing agents may also be employed. Alkali metal borotetrahydrides may be employed as shown in FIG. 2. Of these, sodium borohydride is generally preferred.

The mercaptothiazoline may be hydrolyzed to form a primary thiol as indicated in the figure. The overall reaction sequence thus far is one, therefore, in which the carboxyl group of an initial amino acid is replaced with a mercapto group.

The mercaptothiazoline is readily converted to a primary thiol by a ring opening reaction with a halogen acid, suitably aqueous hydrochloric acid. The reaction temperature may vary from about 60° C. to 160° C. during a period of from eight to twenty hours. One very convenient procedure is to reflux the reaction mixture containing a molar excess of six normal hydrochloric acid for a period of from ten to seventy-two hours.

At the end of the reaction period, the desired product may be recovered as the hydrochloride salt by evaporation at 50° C. to 80° C. under reduced pressure. It is most convenient to isolate the product as the salt since the salt may be employed directly in sequence reactions. However, if for any reason, the free base is desired, it can be obtained by titration to the isoelectric point with, for example, dilute potassium carbonate followed by extraction with a water immiscible organic solvent.

The α-halocarboxylic acids, the secondary halides, used in this invention are produced by diazotization reactions in which the amino group of the corresponding amino acid is replaced with a halide. The presently preferred secondary halides are bromides produced by a diazotization in which nitrosyl bromide is produced by the reaction of dilute sulfuric acid and sodium nitrite in the presence of potassium bromide at a low temperature, e.g., −10° C. to 10° C. The reaction is a typical diazotization reaction, and is so well known that no detailed description would appear to be required. A suitable procedure is described by Pfister et al. in the Journal of the American Chemical Society, 71, 1096 (1949).

Reaction of a primary thiol with a secondary halide, or the alternate reaction of a primary halide with a secondary thiol may be completed utilizing at least equimolar quantities of the reactants in dilute aqueous media under an inert atmosphere at a temperature of from about 20° C. to 60° C. during a period from about ten to thirty hours. To ensure as complete a reaction as possible, and especially to limit interference by competing reactions, such as the reaction in which an amine group, rather than a mercapto group, displaces the halide, it is best to employ a molar excess of the thiol. In fact, the use of from two to three molar excess of this reactant is not unusual.

The presently preferred procedure for isolating the resulting pseudodipeptide is desalting using an ion exchange resin as described by Dreze et al. in Anal. Chin. Acta 11, 554 (1954). The presently preferred resin is Dowex 2-X8.

FIG. 3 illustrates a reaction sequence in which an amino substituted primary halide reacts with an α-mercaptocarboxylic acid, i.e., a secondary thiol.

The starting amino alcohol may be prepared as described above and then converted to a primary halide.

In order to prepare primary halides, the amino alcohols prepared as indicated above are reacted with halogen substituting agents. These may include any of a variety of such agents known to those skilled in the art. However, the preferred agents are those indicated in the figure, that is thionyl chloride or bromide or 48% aqueous hydrogen bromide.

The reaction with the thionyl halide may be effected without a solvent, but for better control the reaction normally takes place in a reaction inert polar solvent, typically anhydrous dimethyl formamide or dimethyl sulfoxide. Reaction is usually complete at the end of approximately one to three hours at reflux utilizing at least a molar quantity of the thionyl halide, but normally at least a 10% molar excess of the reagent.

At the end of the reaction period, the excess thionyl halide is decomposed by the addition of water. The resulting mixture is neutralized with dilute aqueous sodium bicarbonate and extracted with a water immiscible organic solvent, such as diethyl ether. The nonaqueous layer is dried suitably over anhydrous magnesium sulfate, filtered, and the desired product recovered by evaporation of the solvent under vacuum.

The reaction with hydrogen bromide may be carried out in an aqueous medium utilizing a molar excess of HBr under reflux during a period of approximately one to three hours. The desired reaction product may be recovered as described in the immediately proceding paragraphs, except, of course, that there is no necessity for decomposing excess reagent.

The secondary thiol is prepared from a secondary halide obtained through the diazotization procedure described above.

The secondary halide may be converted to the desired thiol figure by reaction with thiourea in an aqueous-alkanol medium in the presence of dilute base. Typically, the reaction is carried out at a temperature of from about 70° C. to 100° C. in 95% aqueous ethanol during a period of from about one to four hours. Equimolar quantities of the reactants may be employed, but it is generally preferred to use an excess of thiourea so as to ensure as complete a reaction as possible. The preferred alkaline reagent is sodium hydroxide, and it is used in essentially catalytic quantities, e.g., up to about five molar percent.

An intermediate isothiouronium halide is formed, but need not be isolated. Instead, additional aqueous alkali is added to the reaction medium, and the resulting mixture heated at from about 70° to 100° C. for an additional one to four hours.

The resulting product is conveniently isolated by extraction with a water immiscible organic solvent such as ether after neutralization with dilute acid, e.g. dilute hydrochloric acid. The product is obtained from organic solution after drying over an anhydrous reagent, filtering, and removal of the solvent under vacuum. The procedure is described in somewhat more detail in Org. Syn., Coll. Vol. 4, 401 (1963).

The primary halide is then reacted with the secondary thiol as described above.

FIG. 4 illustrates another procedure for preparing a primary thiol for reaction with a secondary halide. The preferred procedure is to replace a halogen of a primary halide with trithiocarbonate, and to thereafter decompose the resulting thioester with acid. The procedure is described in detail by Martin et al. in J. Org. Chem. 33, 1275 (1968). It is a most convenient synthetic tool.

In the usual procedure for carrying out the reaction, the trithiocarbonate is formed by reaction of carbon disulfide and sodium sulfide in aqueous alkali, for example 10% sodium hydroxide. The primary halide is added to the trithiocarbonate reagent at a temperature of from about 20° C. to 60° C. The reaction mixture is maintained at from about 20° C. to 60° C. for from about five to fifteen hours to form the thioester.

The thioester need not be isolated. In fact, it is usually most convenient not to do so. Instead, the pH of the reaction medium is reduced to about two to three by the addition of an acid suitably a mineral acid, such as hydrochloric acid. The primary thiol which forms may be isolated by extraction with a water immiscible organic solvent, such as ether, drying over anhydrous reagent, filtering, and removal of the solvent under vacuum.

The procedure for reacting the primary thiol with the secondary halide has been described above.

The key reaction in the synthesis shown in FIG. 5 is the conversion of a primary halide to a primary thiol with thiourea. The reaction conditions for preparing the primary thiol by this route are essentially the same as described above for the preparation of a secondary thiol.

FIG. 6 illustrates somewhat more specifically the reaction sequence which is the last step of the synthetic sequence shown in FIG. 2. It illustrates the preparation of a secondary halide by diazotization, and its conversion into a pseudodipeptide by reaction with a primary thiol.

FIG. 7 illustrates a corollary of the reaction sequence shown in FIG. 4. It illustrates the preparation of a secondary thiol by the same procedure utilized for the preparation of a primary thiol in the synthesis of FIG. 4.

Figure 1:
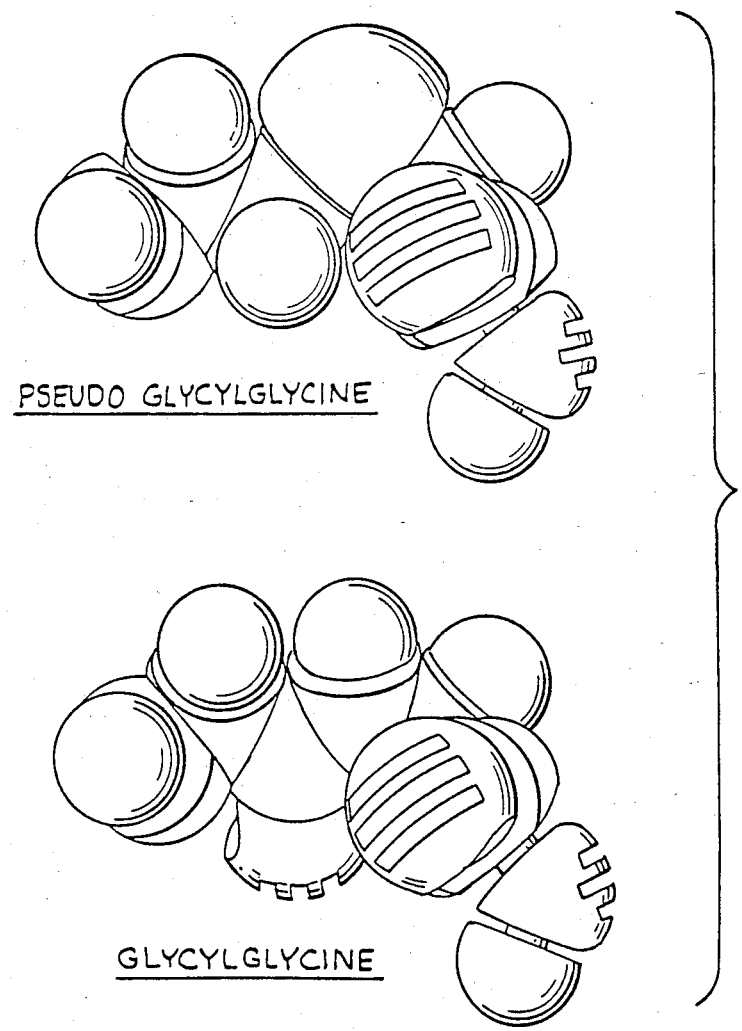

The synthesis shown in FIG. 8 is a corollary of the synthesis of FIG. 5 and illustrates the fact that the thiourea procedure for preparing primary thiols is also applicable to the preparation of secondary thiols.

FIG. 9 illustrates a process of the invention in which an amino alcohol, blocked at the amino group is reacted with tosyl chloride, and the resulting product reacted with the dialkali metal salt of an α-mercapto-carboxylic acid. The blocking group may be any of a large number of known amino blocking groups such as the t-butoxy group or the carbobenzoxy group. These groups are presently preferred, but any of a number of others may be employed. The selection of the blocking group will generally be made on the basis of subsequent reactions in which the resulting dipeptide will be involved, all in accordance with principles well known to those skilled in the art.

For the preparation of the tosyl ester, the blocked amino alcohol is reacted with a tosyl halide, preferably tosyl chloride in a suitable solvent at a temperature of from −20° C. to 10° C. for a period of from one to one-hundred hours.

A molar excess of the tosyl compound is normally employed to insure as complete a reaction as possible. Thus, from a molar equivalent to a molar excess of at least two, based on the number of moles of amino alcohol will normally be employed.

The reaction is one which generates a halogen acid, so it is normally carried out in the presence of a basic reagent which neutralizes the acid as it is produced. Normally the alkaline reagent chosen will be one which is soluble in the selected solvent. As will be apparent to those skilled in the art, the selected solvent must be reaction inert. Thus, neither water, ethyl alcohol, or any other solvent with an active hydrogen could be used as a solvent since they would react with the tosyl chloride.

The most preferred solvent is pyridine, since the the liquid combines the ability to neutralize the hydrogen halide with its ability to dissolve the reactants. Additionally, it is readily removed at the end of the reaction period because it is soluble in water. Thus it is possible to isolate the reaction easily since the solvent is soluble in water and the reaction product is soluble in organic solvents.

Conversion of the tosyl derivative to a pseudodipeptide is accomplished by reaction with, for example, the disodium or dipotassium salt of glycine, alanine, leucine or isolucine, in a reaction inert solvent under alkaline conditions at a temperature of from about 20° C. to 75° C. for from two to twelve hours. Normally a molar excess of the mercapto compound will be employed to insure complete reaction. However, if the mercapto compound is the more expensive of the two reactants an excess of the tosyl derivative can be used. Therefore, based on the number of moles of the tosyl derivative, the number of moles of tosyl compound per mercapto compound can be from 0.5 to 3 moles. Typically useful organic solvents include polar solvents such as dimethylformamide and lower alkanols including methanol and ethanol.

FIG. 10 illustrates a procedure in which the tosyl derivative of the selected amino alcohol is cyclized to a cyclic imine. This is accomplished in an aqueous media under strongly alkaline conditions, i.e., a pH of at least 11 to 13, at a temperature of from 25° C. to 75° C. for a period of from one to four hours. Alkali metal hydroxides are suitable alkaline reagents.

The substituted imine is linked to the selected alpha mercapto acid by reaction in aqueous alkali at a temperature of from 20° C. to 50° C. for a period of from 0.5 to 3 hours. The mixture is acidified, suitably with a mineral acid at the end of the reaction period. The pseudopeptide can be recovered from the aqueous medium by extraction with an organic solvent.

FIGS. 11 and 12 illustrate the application of the reactions described above to specific pseudopeptides. FIG. 11 illustrates the production of Boc-Phe Ψ Leu, and FIG. 12 Leu Ψ Gly.

In the synthesis of Boc-Phe Ψ Leu. phenylalanine is first reduced to the corresponding amino alcohol with borane, and the amino group is blocked with a t-Boc radical. The blocked amino alcohol is converted to the O-tosyl derivative and reacted with the disodium salt of leucine.

For the procedure illustrated in FIG. 12, leucine is converted to 4-isobutyl-2-mercapto-thiazoline by reaction with carbon disulfide in KOH-EtOH at 40° C. for 24 hours. The thiazoline ring is opened with acid to form the thioleucinol acid salt, and this compound is reacted with alpha-iodoacetic acid to form the desired product.

Those skilled in the art will recognize that several of the reactions described in connection with the synthesis illustrated in FIGS. 2 through 12 may involve inversion. The course of the various reactions can be readily followed by conventional techniques. Thus, if a D-pseudopeptide within the scope of this invention is to be synthesized, it may be necessary to utilize a starting compound with an L-configuration. Similarly, the preparation of an L-pseudopeptide may require that the starting compound have a D-configuration.

A large number of pseudopeptides have been prepared by the procedures described above. Table 1 lists some of them and their physical constants.

TABLE 1

Characterization of Gly Ψ Leu, Gly Ψ Ile, and their Stereoisomers

| Dipeptide Analog | Mp °C. (decomp.) | $[\alpha]_D^{22}$ (c = 2, H$_2$O) | Analysis (%) - Found Calcd. for C$_8$H$_{17}$NO$_2$S* | | | |
|---|---|---|---|---|---|---|
| | | | C | H | N | S |
| Gly Ψ Leu | 214–216 | −23.2 ± 1.2° | 50.10 | 9.08 | 7.20 | 16.60 |
| Gly Ψ$_R$ Leu | 221–224 | +24.1 ± 1.3° | 50.56 | 9.13 | 7.37 | 16.45 |
| Gly Ψ Ile | 218–220 | −57.2 ± 1.0° | 50.57 | 9.04 | 7.35 | 16.65 |
| Gly Ψ$_R$Ile | 210–213 | +37.9 ± 1.2° | 50.40 | 8.96 | 7.36 | 16.81 |

*C, 50.23; H, 8.96; N, 7.32; S, 16.76

A particular feature of this invention is the fact that a pseudodipeptide, once prepared, can be chemically treated like a normal peptide. Thus, the chain length can be increased at both the amino and the carboxyl termini by the usual methods employed in peptide syntheses.

Perhaps the most convenient procedure is the Merrifield technique in which an amino acid, peptide or pseudopeptide is bound to a resin particle through an ester linkage. Successive amino acides, peptides or pseudopeptides are then added to the growing molecule by techniques well known to those skilled in the art. Once the desired molecule is generated, it is cleaved from the resin. One useful reagent for cleavage is anhydrous liquid hydrogen fluoride in a reaction inert solvent at 0° C.

The following non-limiting examples are given by way of illustration only.

EXAMPLE 1

Gly Ψ Leu

2-Bromo-4-Methyl-Pentanoic Acid

A total of 50 g. of D-Leu are taken up in 1200 ml. of 2.5 N sulfuric acid containing 250 g. of potassium bromide. The mixture is cooled to 0° C. and stirred while adding 65.5 g. of sodium nitrite in small portions over a period of 1½ hours. The solution is stirred for an additional hour at 0° C., and then heated to 25° C. and stirred another hour. The mixture is extracted with ether, the ether layer separated, washed with water, and dried over anhydrous sodium sulfate to give the desired product.

2-Mercapto-4-Methyl-Pentanoic Acid

A total of 1.25 g. (6.5 mmoles) of the product prepared above is taken up in 2 ml. of water. Sufficient 1 N sodium hydroxide is added to dissolve the bromo acid. To this mixture, there is added 5 ml. of 40% sodium thiocarbonate and the vessel is closed and allowed to stand at room temperature for 24 hours. At the end of this period, the solution is acidified with 18 N. sulfuric acid, and extracted with 2 10 ml. portions of ethyl ether. The combined extracts are dried over anhydrous magnesium sulfate and filtered. The filtrate is concentrated to approximately half its volume and chromatographed on a silica gel column (2.2×30 cm). The original solution is eluted with 150 ml. of ethyl ether, and the product recovered by evaporation of the solvent in the eluate. The yield is approximately 34%. The $R_f$ values (TLC) are 0.88 and 1.0 on silica gel and cellulose plates (n-butanol/acetic acid/water-12/3/5).

Gly Ψ Leu

Ethyleneimine (30 mmoles) is added to 2.2 mmoles of the previous product in 10 ml. of 0.5 N sodium bicarbonate. This solution is maintained at about 20° C. for 2 hours, and acidified with 12 N hydrochloric acid. It is then extracted several times with ether, and the extracts discarded. The aqueous solution is desalted on a Dowex 2 X8 column according to the procedure of Dreze et al. The acetic acid fractions are recovered, and the product isolated by evaporation. The residue is recrystallized from 50% ethanol to give a product with an $R_f$ value of 0.82 by TLC on cellulose in the same butanol/acetic acid/water mixture previously described. The specific rotation, $[\alpha]_D^{22}$ is $-16.3°$.

Gly Ψ Leu

A total of 5.3 g. (27 mmoles) of the bromo acid previously described is dissolved in 530 ml. of nitrogen-purged 0.5 M sodium bicarbonate and 9.2 g. (81 mmoles) of 2-mercaptoethylamine hydrochloride is added. The reaction vessel is flushed with nitrogen for one hour and sealed. It is then allowed to stand at room temperature for 24 hours while the desired product forms. The solution is acidified with 6 N HCl and extracted twice with ether. The ether extracts are discarded, the aqueous portion neutralized with 2 N sodium hydroxide, and diluted to 2 liters with deionized water. The solution is desalted on a 5.5×30 cm. column of Dowex 2 X8 resin according to the method of Dreze et al. The acetic acid fractions are pooled and evaporated to dryness under reduced pressure, the residue triturated with 20 ml. of acetone, and crystallized from 47.5% ethanol to give white needles of the desired product (yield 2.34 g., 44.5%, mp 205°–210° C. with decomposition).

These same procedures are utilized to prepare Gly Ψ Ile substituting D-alloisoleucine for the D-leucine.

It is observed that in the course of these reactions the halogen replaces the original amino group without inversion of configuration. Inversion does take place during the replacement of the bromine. Thus, the amino acid residues of the pseudopeptides are in the L-form. Analoqous pseudopeptides in which the components are in the D-form are prepared utilizing the corresponding L-form of the starting amino acids.

EXAMPLE 2

Phe Ψ His

2-Mercapto-4-Benzyl-Thiazoline

A total of 75 mmoles of Phe in 225 mmoles of ethanol containing 300 mmoles of carbon disulfide and 75 mmoles of solid potassium hydroxide is added with stirring while maintaining the temperature below 40° C. The temperature is then raised to 40° C. and the reaction mixture held in a closed vessel for 12 hours. At the end of this period, the alcohol and carbon disulfide are removed by rotary evaporation. The residue is suspended in a small amount of cold water, and the product recrystallized from the water-ethanol mixture.

2-Mercapto-1-Benzyl-Ethylamine

A total of 4 g. of the mercaptothiazoline is taken up in 25 ml. of 12 N HCl and heated under reflux for five hours at 155° C. At the end of this period, the excess acid is removed by rotary evaporation. The desired product is recovered as the hydrochloride and recrystallized from aqueous ethanol Phe Ψ His This product is prepared from α-bromo-β-(5-imidazolyl) propionic acid and 2-mercapto-1-benzyl-ethylamine by reaction in the presence of sodium carbonate utilizing the procedure described for the analogous reaction involving 2-mercaptoethylamine as described in Example 1.

The pseudopeptide Leu Ψ Leu is similarly prepared utilizing as reactants an isobutyl substituted ethanolamine and an isobutyl substituted 2-mercapto ethylamine.

Ala Ψ Ala is similarly prepared from 4-methyl-2-mercapto thiazoline [Gabriel and Ohle Ber., 50, 804 (1917)]and α-bromo-prppionic acid.

The procedures described in these examples are utilized to prepare the following pseudodipeptides:

| | | | |
|---|---|---|---|
| Trp Ψ Gly | Arg Ψ Val | Phe Ψ Tyr | Met Ψ Lys |
| Gln Ψ Lys | Lys Ψ His | Arg Ψ Gly | Gly Ψ Lys |
| Gln Ψ Arg | Arg Ψ Val | Lys Ψ Tyr | Lys Ψ Arg |
| Arg Ψ Thr | Arg Ψ Lys | Tyr Ψ Leu | Phe Ψ Arg |
| Arg Ψ Leu | Arg Ψ Val | Lys Ψ Tyr | Arg Ψ Pro |
| Tyr Ψ Gly | Lys Ψ Lys | Tyr Ψ Leu | Phe Ψ Ser |
| Phe Ψ Met | Lys Ψ Leu | Pro Ψ Arg | Tyr Ψ Glu |
| Phe Ψ Leu | Phe Ψ Trp | Tyr Ψ Phe | Tyr Ψ Gly |

EXAMPLE 3

Solid Phase Synthesis of

Ac-Pro-Gin-Gly Ψ Leu-Ala-Gly-Leu Ψ Z Orn-Gly-NH₂

Synthesis of this pseudopeptides is accomplished using the peptide shaking apparatus with a medium reaction vessel described by Stewart and Yound (Solid Phase Peptide Synthesis, W. H. Freeman and Company, 1969).

Boc-Gly-Resin (4 g.) containing 0.24 mmoles Gly per g. of resin is used as the starting material. the following schedule is employed in each cycle of Boc-A.A. or Boc pseudodipeptide additions to the resin.

| Step | Reagent or Solvent | No. Times | Vol (ml) | Time (min) |
|---|---|---|---|---|
| 1 | CH₂Cl₂ | 3 | 40 | 1 |
| 2a | 40% TFA/CH₂Cl₂/Anisole | 1 | 40 | 20 |
| 2b | TFA/CH₂Cl₂/Anisole | 1 | 40 | 1 |
| 3 | CH₂Cl₂ | 5 | 40 | 1 |
| 4 | (i-Pr)₂Net/CH₂Cl₂ | 2 | 40 | 2 |
| 5 | CH₂Cl₂ | 4 | 40 | 1 |
| 6 | Boc-A.A., (3 eq.) | 1 | 15 | 20 |
| 7 | Box-A.A. line flush | 1 | 5 | — |
| 8 | DCC (2.7 eq.) | 1 | 15 | 90 |
| 9 | CH₂Cl₂ | 2 | 40 | 1 |
| 10 | EtOH | 2 | 40 | 1 |
| 11 | CH₂Cl₂ | 4 | 40 | 1 |
| 12 | Boc-A.A. + | 1 | 15 | — |
| 13 | Boc-A.A. line flush | 1 | 15 | — |

-continued

| Step | Reagent or Solvent | No. Times | Vol (ml) | Time (min) |
|---|---|---|---|---|
| 14 | DCC | 1 | 15 | — |
| 15 | DCC line flush & coupling | 1 | 5 | 90 |
| 16 | CH$_2$Cl$_2$ | 3 | 40 | 1 |
| 17 | EtOH | 3 | 40 | 1 |
| 18 | DMF | 3 | 40 | 2 |
| 19 | Ac$_2$O 4 ml. | 1 | 50 | 50 |
| 20 | DMF | 2 | 40 | 2 |
| 21 | EtOH | 3 | 40 | 2 |

From the schedule, it can be seen that a double coupling with acetylation of any residual amino group is employed in this synthesis. At each step 3 equivalents of amino acid or pseudodipeptide are employed per equivalent of Boc Gly resin present.

Before coupling of Boc-Leu Ψ Z Orn and Boc-Gly Ψ Leu, these substances are released from their corresponding dicyclohexylamine salts by suspending 2.5 g. of the salt in 10 ml. water. Citric acid (1 M) is slowly added until the powder is liquified. An equal volume of ether is added. After thorough mixing, the ether layer is separated. The ether layer is washed once with water, and then dried over sodium sulfate. The ether is removed at reduced pressure, and the sample is dried overnight to give the free pseudodipeptide. Boc-pseudodipeptides are coupled in the same manner as the amino acids.

In the case of Gln addition, the Boc Gln-p-nitrophenyl ester is employed at a 4 fold molar excess. DMF is substituted for methylene chloride in the coupling, washing and acetylation steps. A coupling time of 19 hrs. is used for each cycle of nitrophenyl ester. After Pro is added, the deprotection steps and acetylation steps are performed, and the completed resin coupled peptide released from the resin with MeOH and triethylamine to give the methyl ester which is then treated with anhydrous ammonia in dry methanol to give the amide.

Conversion of

Ac-Pro-Gln-Gly Ψ Leu-Ala-Gly-Leu Ψ Z Orn-Gly-NH$_2$

Ac-Pro-Gln-Gly Ψ Leu-Ala-Gly-Leu Ψ Arg-Gly-NH$_2$

The peptide amide containing Leu Ψ Z Orn is dried rigorously under vacuum, and then subjected to anhydrous liquid hydrogen fluoride in the presence of 100 equivalents of methyl ethyl sulfide, with stirring, for 30 min. at 0° C. The peptide is chromatographed on a column of Sephadex G-100 in 10% aqueous acetic acid. The fractions containing the deprotected peptide are combined and lyophilized to give Ac-Pro-Gln-Gly Ψ Leu-Ala-Gly-Leu Ψ Orn-Gly-NH$_2$.

This peptide is then treated with O-methyl isourea according to the method of Merrifield (Cosand and Merrifield, Proc. Natl. Acad. Sci. USA 74, 2771-2775 (1977) to give the desired Ac-Pro-Gln-Gly Ψ Leu-Ala-Gly-Leu Ψ Arg-Gly-NH$_2$

EXAMPLE 4

Ac-Pro-Gln-Gly Ψ Leu-Ala-Gly-Leu-Arg-NH$_2$

The following table summarizes the reactions for the preparation of the title compound. The values in the right hand column show the amino acid composition at each stage in the synthesis. The values for the pseudodipeptide which elutes in the position of Phe using a 4.5 hr citrate buffer elution program are determined after HCl-propionic acid hydrolysis using cysteamine as a scavanger. Appropriate control analyses are performed in the absence of pseudopeptide.

The section following the table describes the various steps in the synthesis.

In the table and description Aoc signifies a t-amyloxycarbonyl group.

Collagenase activity is inhibited by the presence of this pseudooctapeptide which masquerades as a segment of the natural collagen molecule when the enzyme is assayed using the octapeptde with the natural sequence as a substrate.

TABLE 3

Benz. Resin
↓ Aoc—Arg(Tos), DCC

Aoc—Arg(Tos)—Benz. Resin
↓ Boc—Leu, DCC

Boc—Leu—Arg(Tos)—Benz. Resin     Leu 1.38
↓ 3 steps     Arg 1.00

| | Ratio of Residues |
|---|---|
| Gly | 1.0 |
| Ala | 0.99 |

Box—Gly Ψ Leu—Ala—Gly—Leu—Arg(Tos)—Benz. Resin

| | |
|---|---|
| Leu | 1.06 |
| Gly Ψ Leu | 1.12 |
| Arg | 0.92 |

↓ TFA 40%, 20 min

Gly Ψ Leu—Ala—Gly—Leu—Arg(Tos)—Benz. Resin

| | |
|---|---|
| Gly | 1.0 |
| Ala | 1.0 |
| Leu | 1.01 |
| Gly Ψ Leu | 1.13 |
| Arg | .94 |

↓ (1) Boc—Gln—NPE
↓ (2) 40% TFA

TABLE 3-continued

| | | |
|---|---|---|
| Gln—Gly Ψ Leu—Ala—Gly—Leu—Arg(Tos)—Benz. Resin (0.276 mmole/g.) | Gln | 0.88 |
| | Gly | 1.0 |
| | Ala | 1.0 |
| ↓ Ac—Pro, DCC | Leu | .99 |
| | Gly Ψ Leu | 1.10 |
| | Arg | .88 |
| Ac—Pro—Gln—Gly Ψ Leu—Ala—Gly—Leu—Arg(Tos)—Benz. Resin (0.243 mmole/g.) | Gln | .86 |
| | Pro | .93 |
| | Gly | 1.0 |
| ↓ HF/Anisole | Ala | 1.0 |
| | Leu | 1.01 |
| | Gly Ψ Leu | 1.08 |
| | Arg | 0.96 |
| Ac—Pro—Gln—Gly Ψ Leu—Ala—Gly—Leu—Arg—NH$_2$ | Gln | 0.86 |
| | Pro | 0.87 |
| | Gly | 1.01 |
| | Ala | 0.97 |
| | Leu | 1.08 |
| | Gly Ψ Leu | 0.73* |
| | Arg | 1.00 |

*Based on hydrolysis in absence of scavenger

Preparation of Boc-Gly Ψ Leu 2-(Tert-butyloxcarbonyloxyimino)-2-phenylacetonitrile (Aldrich, 5.4 g, 22 mmoles) is added to a mixture of Gly φ Leu (3.81 g, 20 mmoles), triethylamine (4.1 ml, 30 mmoles), 12 ml dioxane and 12 ml water at room temperature. The stirred mixture becomes homogeneous within one hour and stirring is continued for ten hours. Water (30 ml) and ethyl acetate (30 ml) are added. The aqueous layer is separated and washed with ethyl acetate (2×40 ml). The aqueous layer is acidified with 5% aqueous citric acid solution and extracted with ethyl acetate. The ethyl acetate extract is washed with saturated aqueous sodium chloride twice and dried over anhydrous sodium sulfate. Removal of drying agent and solvent gave 7.7 g of an oil. The oil is dissolved in 40 ml of ethyl ether and mixed with 7.4 g (40 mmole) of dicyclohexylamine. The resulting suspension is stored at 40° C. for 4 hr prior to collection of the desired salt. The salt is washed with ether and dried in vacuo over phosphorous pentoxide to give 10 g (80% yield based on Gly Ψ Leu) of white crystals. Recrystallization of the dicyclohexylamine salt of Boc-Gly Ψ Leu from methanol:ether (2:1 v/v) giving the purified product, m.p. 143°–144° C. Anal. calcd for $C_{25}H_{48}N_2O_4S$: C, 63.5; H, 10.23; N, 5.93; S, 6.78 Found: C, 63.73; H, 10.48; N, 5.66; S, 6.43

Attachment of C-terminal Amino Acid to the Resin

Benzhydrylamine resin HCl (2.0 g, 0.40 meq/g) is neutralized by stirring 50 ml of 25% triethylamine in methylene chloride for ten minutes. The resin is separated by filtration and washed with additional methylene chloride (25 ml per gm resin). The resin is then suspended in methylene chloride (40 ml) and shaken for 10 hr in the presence of a 2.5 fold molar excess of Aoc-Arg(Tos). After washing with methylene chloride, the remaining unreacted amino groups on the resin are acetylated with a mixture of acetic anhydride and N-methylmorpholine in dimethylformamide. Amino acid analyses of a weighed portion of hydrolyzed Aoc-Arg(Tos) resin gives a value of 0.24 mmole of arginine released per gm resin.

Chain Elongation of Double Cycle Addition and Acetylation

After the first amino acid is coupled to the resin, the remaining amino acids are added sequentially by the following procedures: The resin is washed thrice with methylene chloride and then prewashed with trifluoroacetic acid-anisole-methylene chloride (40:2:60, v/v). Amino groups are released by shaking with a TFA solution of the same composition for 20 minutes. Five washings with methylene chloride are followed by two washings with 7% (v/v) N,N diisopropylethylamine in methylene chloride. Excess amine is removed by washing five times with methylene chloride. t-Butyloxycarbonyl amino acid (2.5 molar excess) is added to the reaction vessel in methylene chloride Dicyclohexylcarbodiimide (2.3 molar excess) is added in methylene chloride (final volume of 40 ml). The reaction vessel is shaken for two hr. Two washings with methylene chloride are followed by two ethanol washings. The five methylene chloride prewashes, as well as the coupling steps, are repeated. After three washings with dimethylformamide, residual unacylated amino groups on the resin are acetylated with a mixture of acetic anhydride (4 ml), N-methylmorpholine (2 ml) and dimethylformamide (34 ml) during 20 minutes of shaking. The double cycle of coupling is complete after three washings with dimethylformamide followed by three washings with ethanol. The double cycle-acetylation sequence described is followed for addition of each amino acid residue including acetyl proline, but with the exception of Gln. Gln is introduced (double cycle) as t-Boc-p-nitrophenyl ester in dimethylformamide (omitting dicyclohexylcarbodiimide) and a ten hr. reaction time is used instead of two hr. The progress of the synthesis is followed by frequent hydrolysis and analysis of the growing peptide-resin.

Addition of Boc-Gly Ψ Leu

Release of Boc-Gly Ψ Leu from the dicyclohexylamine salt is accomplished by suspending the salt (2 g) in 30 ml of a mixture of ethyl ether and water(1:1, v/v). Citric acid (1 M) is added until all the solid dissolves. The ether layer is separated, washed with water and then dried over anhydrous sodium sulfate. The sodium sulfate is removed by filtration and the ether removed by rotary evaporation. The residual oil is dried in a vacuum desiccator to constant weight. The yield is 1.45 g (97%). Boc-Gly Ψ Leu is added to peptide-resin following the procedure for Boc-amino acids described above.

Release and deprotection of peptide from benzhdrylamine resin product

The tosylated benzhydrylamine resin-peptide (2.0 gm) is treated with 20 ml of CoF$_3$-dried HF in the presence of 2.0 ml of anisole for one hr at 0° C. After removal of HF under reduced pressure, the resin is dried overnight under vacuum. The released, deprotected peptide is extracted from the resin with 60 ml of 7% acetic acid. The filtered extract is washed with separate 30 ml portions of ethyl ether and ethyl acetate to remove anisole. The solution is lyophilized, the residue dissolved in 0.2 M acetic acid and lyophilized again. The crude peptide amide is chromatographed on Sephadex G-15 in 0.5 M acetic acid. The major component as determined by Sakaguchi assay is lyophilized to give crude peptide amide weighing 334 mg (yield 80%). The product is further purified by partition and/or carboxymethylcellulose-chromatography.

Partition Chromatography on Sephadex G-25

A column (73×2.5 cm) of Sephadex G-25 (fine grade) is packed in water. The column is equilibrated with the lower phase of the solvent mixture of n-butanol:pyridine: 0.1% aqueous acetic acid (5:3:11, v/v) (15) and then followed by the upper phase of the same solvent system (16) at a flow rate of about 1 cm/min. The peptide (55 mg) is dissolved in the upper phase (5 ml) and chromatographed by elution with the upper phase. The fractions containing peptide are detected by the quantitative Sakaguchi method (17). Fractions of the major component are pooled, diluted with an equal volume of water and concentrated by rotorary evaporation under reduced pressure. The concentrate is lyophilized to give a white powder (32 mg (58%)).

EXAMPLE 5

BOC-PHE Ψ GLY DICYCLOHEXYLAMINE SALT

This compound can be freed from the dicyclohexylamine moiety and incorporated into a larger peptide by the procedures illustrated or discussed herein. Alternatively, the Boc group can be removed by treatment with HF as described in the last section of Example 4. The resulting peudodipeptide can serve as a surrogate for Phe-Gly.

Preparation of Boc-phenylalaninol

To a mixture of 10 ml of water and 10 ml of dioxane are added 3 grams (20 mmol) of phenylalaninol and 20 mmole of t-butyloxycarbonyl azide and sufficient sodium hydroxide solution (1 N) to raise the pH to 8.0. The reaction mixture is stirred for 24 hours after which 50 ml of ethyl ether are added, and the mixture cooled to 0° C. Solid citric acid is added until the pH is lowered to 3.5 The aqueous layer is extracted twice with 25 ml of ether. The combined ether extracts are washed twice with 25 ml portions of 5% citric acid, followed by three washes with saturated sodium chloride solution. The organic layer is dried over anhydrous sodium sulfate. Removal of solvent under reduced pressure gives 5.4 grams of oil. The oil is treated with hot hexane to give 4.1 grams of white solid (needles; 81%). The crude product is recrystallized from 100 ml hot hexane containing 10 drops of ether. A white solid with melting point 93° to 94° C. is obtained (2.8 grams).

Preparation of Boc-phenylalaninol Tosylate

To a solution of 2.5 grams (0.01 mole) of Boc-phenylalaninol in 10 ml of dry pyridine cooled to −10° is added 3.8 grams (0.02 mole) of tosyl chloride. This solution is left in a freezer overnight until white solid precipitate no longer formed (pyridinium hydrochloride). The mixture is poured into 100 ml each of ice and ether. The organic layer is separated, washed three times each with 5% citric acid and saturated sodium chloride. The solution is dried over anhydrous sodium sulfate, and the solvent removed to give 4.1 grams of white solid, melting point 92 to 93° C. Recrystallization from ether/hexane does not further improve the melting point.

Preparation of Boc-Phe-Ψ-Gly/DCHA Salt

To 0.24 grams (1.8 mmole) of disodium salt of mercaptoacetic acid in 2 ml of dry methanol and 5 ml of dimethylformamide are added 0.6 grams (2.4 mmole) of Boc-phenylalaninol tosylate. This solutin is kept at room temperature for five hours after which the methanol is removed under reduced pressure. The solution is cooled to −5° C. and 25 mil of cooled ethyl acetate added. A 25% solution of citric acid is added to lower the pH to 2. The aqueous layer is extracted three times with 25 ml of ethyl acetate. The combined organic extracts are washed once with 5% citric acid and three times with saturated sodium chloride. The ethyl acetate layer is dried over anhydrous sodium sulfate and the solvent removed under reduced pressure. The oily residue is dissolved in ethyl acetate and excess dicyclohexylamine. Addition of anhydrous diethyl ether results in the preciptitation of the Boc-The-Ψ-Gly/DCHA salt in 58% yield (0.54 grams). This salt is recrystallized from chloroform ether (4:1) to give 0.4 grams of white solid, melting point 140° to 141° C. (43% overall).

EXAMPLE 6

Preparation of Tablets 1000 g. of Gly Ψ Leu and 2000 g. of lactose are thoroughly mixed together and the whole is passed through a 30 mesh sieve.

A paste is separately prepared with 80 g. of cornstarch and 350 ml. of distilled water.

The above mixture is well kneaded with the paste and the mass is passed through a 4 mesh sieve and the resulting globules are dried at 50° C. for 15 hours.

The dried globules are then granulated first on a granulating machine, and passed through a 16 mesh sieve. The grains are covered with a powdery mixture which is prepared by blending 30 g. of calcium stearate, 200 g. of cornstarch and 80 g. of talc, and then passed through a 40 mesh sieve.

Tablets each containing 250 mg. of Gly Ψ Leu are made of the above-obtained granules in accordance with conventional procedures.

EXAMPLE 7

Preparation of Injection 100 g. of the sodium salt Leu Ψ Leu are dissolved in a quantity of distilled pyrogen free water specifically prepared for this purpose, and made up to 5 liters. The solution is made isotonic with addition of a predetermined amount of an aqueous solution of physiological salt and filtered through a millipore bacterial filter.

EXAMPLE 8

Preparation of an Aqueous Solution for Oral Administration

A mixture consisting of:

| Gly Ψ Ile | g | 20.0 |
|---|---|---|
| Cane sugar | g | 100.0 |
| Glycerin | ml | 100.0 |
| Ethyl p-ethoxybenzoate | g | 1.5 |
| Artificial orange essence | ml | 0.2 |
| Essential oil of orange | ml | 1.0 | is added to distilled water to make up 1000 ml. of the final volume.

We claim:

1. Pseudodipeptides useful in the preparation of peptide mimics of a member of the natural catalyst substrate pairs, said pseudodipeptides being selected from the group consisting of Gly Ψ Leu, Phe Ψ His, Gly Ψ Ile, Leu Ψ Leu, Ala Ψ Ala, Tyr Ψ Gly, Arg Ψ Gly, Pro Ψ Gly -NH₂, Lys Ψ Ser, and Arg Ψ Met.

2. A pseudopeptide useful in the treatment of hypertension, selected from the group consisting of Leu Ψ Leu-Val-Tyr, Ac-Phe Ψ His-Leu-Leu-Val-Tyr-Ser-OH, Ac-Phe-His-Leu Ψ Leu-Val-Tyr-Ser-OH and Ac-Phe Ψ His-Leu Ψ Leu-Val-Tyr-Ser-OH and pharmaceutically acceptable salts thereof.

3. A pseudopeptide useful in the treatment of corneal ulceration or rheumatoid arthritis selected from the group consisting of Ac-Pro-Gln-Gly Ψ Ile-Ala-Gly-Gln-Arg-Gly-OEt;Ac-Pro-Gln-Gly Ψ Leu-Ala-Gly-Gln-Arg-Gly-OEt; Ac-Pro-Leu-Gly Ψ Ile-Ala-Gly-Leu-Arg-Gly-OEt; and Ac-Pro-Leu-Gly Ψ Leu-Ala-Gly-Leu-Arg-Gly-OEt; Ac-Pro-Gln-Gly Ψ Ile-Ala-Gly-Gln Ψ Arg; Ac-Pro-Gln-Gly Ψ Ile-Ala-Gly-Leu Ψ Arg, and pharmaceutically acceptable salt thereof.

4. A pseudopetide useful in the treatment of LHRH-related endocrine disorders selected from the group consisting of:

pGlu-His-Trp-Ser-Tyr Ψ Gly-Leu-Arg-Pro-Gly-NH₂
pGlu-His-Trp-Ser-Tyr-Gly-Leu-Arg-Pro Ψ Gly-NH₂
pGlu-His-Trp-Ser-Tyr Ψ Gly-Leu-Arg-Pro Ψ Gly-NH₂
PGlu-His-Trp-Ser-tyr-Gly Ψ Leu-Arg-Pro-Gly-NH₂ and pharmaceutically acceptable salts thereof.

5. A pseudopeptide useful in the relief of pain having the formula Tyr Ψ Gly-Gly-Phe-Leu.

6. A pseudopeptide useful in the treatment of emphysema selected from the group consisting of Ac-Ala-Ala Ψ Ala Oet, Ac-Ala-Ala-Ala Ψ Ala-OEt, and pharmaceutically acceptable slats thereof.

7. A pseudopeptide for the modulation of urokinase activity selected by from the group consisting Ac-Ser-Ile-Arg-Ψ Met-Arg-Asp-Val-OEt, Ac-Glu-Asn-Arg-Lys Ψ Ser -Ser-Ile-Ile-OEt and pharmaceutically acceptable salts thereof.

8. A method of treating hypertension in mammals which comprises administering to said mammal an effective amount of the pseudopeptide of claim 1.

9. A method of treating corneal ulceration or rheumatoid arthritis in mammals which comprises administering to said mammal an effective amount of the pseudopeptide of claim 2.

10. A method of treating LHRH-related endocrine disorders in mammals which comprises administering to said mammals an effective amount of a pseudopeptide of claim 3.

11. A method of relieving pain in mammals which comprises administering to said mammal as effective amount of a pseudopeptide of claim 4.

12. A method of treatment of emphysema in mammals which comprise administering to said mammal an effective amount of a pseudopeptide of claim 5.

13. A method for modulation of urokinase activity in mammals which comprises administering to said mammal an effection amount of a pseudopeptide of claim 6.

* * * * *